United States Patent [19]

Baudouin et al.

[11] 4,225,498
[45] Sep. 30, 1980

[54] PREPARATION OF N-SUBSTITUTED OLIGO-IMIDES

[75] Inventors: Michel Baudouin, Saint-Fons; Jean Abblard, Saint-Didier-au-Mont-d'Or, both of France

[73] Assignee: Rhone-Poulenc Industries, Paris, France

[21] Appl. No.: 931,676

[22] Filed: Aug. 7, 1978

[30] Foreign Application Priority Data

Aug. 9, 1977 [FR] France ................ 77 25215

[51] Int. Cl.² ............... C07D 403/06; C07D 403/02; C07D 207/44
[52] U.S. Cl. ..................... 260/326.26; 260/326 R; 260/326 C; 260/326 E; 260/326 S; 260/326 NS; 260/326 A; 260/326 HL; 260/326.5 FM; 546/256; 546/272; 546/281; 548/143; 548/153; 548/181; 548/193; 548/267; 548/328; 528/170; 528/345
[58] Field of Search ............ 528/170; 260/326.26, 260/326 N, 326 C, 326.5 FM, 326 R

[56] References Cited

U.S. PATENT DOCUMENTS

| | | | |
|---|---|---|---|
| 3,025,300 | 3/1902 | Heubner | 260/326 N |
| 3,406,148 | 10/1968 | Sambeth et al. | 528/170 |
| 3,669,930 | 6/1972 | Asahara et al. | 528/170 |
| 3,729,510 | 4/1973 | Norton | 260/326 N |
| 3,767,671 | 10/1973 | Klebe et al. | 260/326 N |
| 3,855,239 | 12/1974 | Crivello | 260/326.26 |
| 3,862,129 | 1/1975 | Kwiatkowski | 260/326.26 |
| 3,972,087 | 8/1976 | Freedman | 260/250 B |
| 4,118,392 | 10/1978 | Salle et al. | 260/326 N |
| 4,125,535 | 11/1978 | Wolford | 260/326 N |

*Primary Examiner*—Mary C. Lee
*Attorney, Agent, or Firm*—Burns, Doane, Swecker & Mathis

[57] ABSTRACT

N-substituted oligo-imides of the formula:

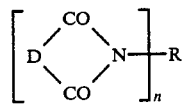

[I]

in which D represents a divalent radical selected from the group comprising:

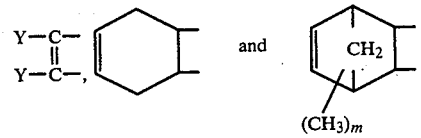

in which m is 0 or 1, Y is hydrogen, chlorine or methyl, n is a positive integer of 5 or less, and R is an organic radical of valency n, containing up to 50 carbon atoms, are prepared by reacting an anhydride of the formula:

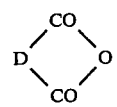

[II]

with an amine of the formula:

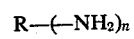

[III]

in which formulae D, R and n are as above defined, said reaction being carried out in the presence of a catalyst system comprising a mixture of a compound (1) and a compound (2), (1) being a strong inorganic or organic oxygen-containing acid and (2) being an ammonium salt of such acid, said ammonium salt being di-, tri- or, preferably, tetra-substituted on the nitrogen atom by organic radicals.

21 Claims, No Drawings

PREPARATION OF N-SUBSTITUTED OLIGO-IMIDES

SUMMARY OF THE INVENTION

The present invention relates to a process for the preparation of N-substituted oligo-imides from dicarboxylic acid anhydrides and an amine.

The N-substituted oligo-imides prepared according to the invention are, more especially, compounds of the formula:

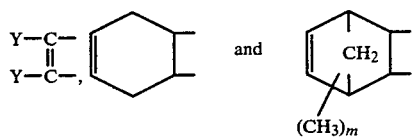
[I]

in which D represents a divalent radical selected from the group comprising:

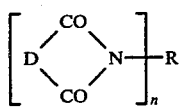 and 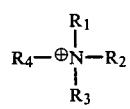

(CH$_3$)$_m$ in which m is 0 or 1, Y is hydrogen, chlorine or methyl, n is a positive integer of 5 or less, and R is an organic radical of valency n, containing up to 50 carbon atoms.

The radical R can be purely hydrocarbon in nature, or can contain one or more heteroatoms; the radical R can thus contain a plurality of hydrocarbon groups or heterocyclic rings joined or linked together by heteroatoms or heterotomic groups; same can also contain substituents such as: halogen atoms and nitro, amino, hydroxyl, alkoxy and alkylthio groups, in addition, of course, to carbonyl groups.

The invention, particularly, relates to a process for the preparation of oligo-imides of the formula I, from an anhydride of the formula:

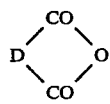
[II]

and an amine of the formula:

R⫲(NH$_2$)$_n$  [III]

in which formulae D, R and n are as above defined, the said process being characterized in that the reaction is carried out in the presence of a catalyst system comprising a mixture of a compound (1) and a compound (2), (1) denoting a strong inorganic or organic oxygen-containing acid and (2) denoting an ammonium salt of this acid, said ammonium salt being of the type in which the ammonium is di-, tri- or, preferably, tetra-substituted on the nitrogen atom by organic radicals.

DETAILED DESCRIPTION OF THE INVENTION

By the term strong inorganic or organic oxygen-containing acid (1), there is intended an oxygen-containing mono- or polyacid in which at least one of the acid functions possesses an ionization constant in water, pKa, which is 3 or less. Exemplary of acids of this type, there are mentioned: from among the inorganic acids, sulfuric, orthophosphoric and pyrophosphoric acids; from among the organic acids, organo-sulfonic acids, in particular para-toluenesulfonic, methanesulfonic and naphthalenesulfonic acids, organo-phosphonic acids, in particular monoalkyl- or monoaryl-phosphonic acids, such as methylphosphonic or benzenephosphonic acid, and strong mono- or polycarboxylic acids such as dihalogeno- and trihalogeno- (especially chloro- and fluoro-) -acetic or -propionic acids.

According to the invention, the organic sulfonic acids, and more particularly, alkyl- or aryl-sulfonic acids, such as methane sulfonic, para-toluenesulfonic and benzenesulfonic acids, are preferably employed as the strong acid (1).

As the ammonium salt (2), a salt is therefore used in which the anionic moiety corresponds to the acid (1) [namely, the anionic moiety yields the acid (1) by addition of the H$^+$ ions required for electrical neutrality] and in which the cationic moiety has the formula:

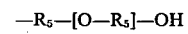
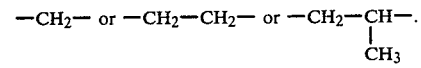
[IV]

in which R$_1$, R$_2$, R$_3$ and R$_4$ represent identical or different organic radicals in which the free valency is borne by a carbon atom, it being possible for R$_1$ and R$_2$ to optionally represent the hydrogen atom and for two or more of these various radicals to optionally form one individual divalent radical [if there be two radicals] or one individual trivalent radical [if there be three radicals] or two individual divalent radicals [if there be two pairs of radicals]. However, quaternary ammonium salts are preferred as the salt (2).

More specifically, R$_1$, R$_2$, R$_3$ and R$_4$ can represent saturated or unsaturated aliphatic (linear or branched), cycloaliphatic or aromatic (of the aryl or arylaliphatic type) hydrocarbon radicals, or radicals containing several oxyalkylene linkages, for example, radicals of the formula:

—R$_5$—[O—R$_5$]$_t$—OH in which t is between 1 and 10 and R$_5$ represents the radical:

—CH$_2$— or —CH$_2$—CH$_2$— or —CH$_2$—CH—.
$\phantom{xxxxxxxxxxxxxxxxxxxxxxxxxx}$CH$_3$ At least two of the radicals R$_1$, R$_2$, R$_3$ and R$_4$ can represent alkylene or oxydialkylene groups.

The various radicals R$_1$, R$_2$, R$_3$ and R$_4$ can optionally contain other ammonium groups, as in the case of salts in which the cation has the formula:

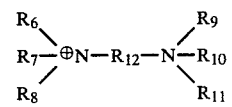
(V)

in which R$_6$, R$_7$, R$_8$, R$_9$, R$_{10}$ and R$_{11}$ represent hydrocarbon radicals or radicals containing oxyalkylene groups, such as defined above for R$_1$, R$_2$, R$_3$ and R$_4$, and R$_{12}$ is a divalent, aliphatic or aromatic (especially arylaliphatic) hydrocarbon radical in which the carbon chain or chains can be interrupted by oxygen atoms, the free valencies of the radical $R_{12}$ being borne by carbon atoms which are aliphatic in nature, and it being possible for one or more pairs of the radicals $R_6$, $R_7$, $R_8$, $R_9$, $R_{10}$ and $R_{11}$ to form individual divalent alkylene or oxyalkylene radicals.

The total number of carbon atoms in the cationic moiety of the salt (2) is typically less than 50, and preferably between 6 and 42.

More particularly, the following are noted as illustrative of the ammonium salts (2) according to the invention: tetramethylammonium, tetraethylammonium, tetrapropylammonium, tetrahexylammonium, tetraoctylammonium, tetradodecylammonium, tetrabutylammonium, tributyldodecylammonium, trimethyldodecylammonium, trimethyltetradecylammonium, trimethylhexadecylammonium, trimethyloctadecylammonium, trimethyloctadecen-9-ylammonium, trimethyloctadien-9,12-ylammonium, trimethyloctadecatrien-9,12,15-ylammonium, trimethyleicosylammonium, trimethyldocosylammonium, trimethyldocosen-13-ylammonium, triethyloctadecylammonium, triethylhexylammonium, dimethylbenzyldodecylammonium, diethylbenzyldodecylammonium, dimethyldioctadecylammonium, diethyldioctadecylammonium, dimethylditetradecylammonium, diethylditetradecylammonium, dimethyldidodecylammonium, diethyldidodecylammonium, dimethyldihexadecylammonium, methyltributylammonium, methyltriethylammonium, methyltridodecylammonium, ethyltributylammonium, ethyltrioctylammonium and ethyltridodecylammonium salts.

The catalyst system (1)/(2) according to the invention is prepared by mixing a strong inorganic or organic acid (1) with the salt (2) or the amine which, together with (1), can yield the salt (2); they can be mixed together either before mixing them with the reactants, or in the reaction medium; of course, it is possible to use a catalyst system comprising several acids (1) and several salts (2); thus, if an acid (1) is mixed with an ammonium salt derived from another acid (1'), and if these acids (1) and (1') have a similar acidity, an equilibrium will automatically be established in the reaction medium and a mixture of the acids (1) and (1') and their corresponding salts (2) and (2') will thereby be obtained.

Taking account of the meanings indicated previously for the symbol D, the anhydride can be, in particular, maleic anhydride, which is the preferred, chloromaleic anhydride, citraconic anhydride, tetrahydrophthalic anhydride or endomethylenetetrahydrophthalic anhydride.

When n is other than 1, the amine of the formula (III) is a polyamine which can be a diamine or a compound containing up to 5 primary amino groups.

In the case of the diamines, it is representative to use compounds having the general formula:

$$H_2N-E-NH_2 \qquad [IV]$$

in which the symbol E represents a divalent radical containing from 2 to 30 carbon atoms. This radical can be, in particular, a linear or branched alkylene radical having fewer than 13 carbon atoms, a phenylene or cyclohexylene radical or a radical of the formula:

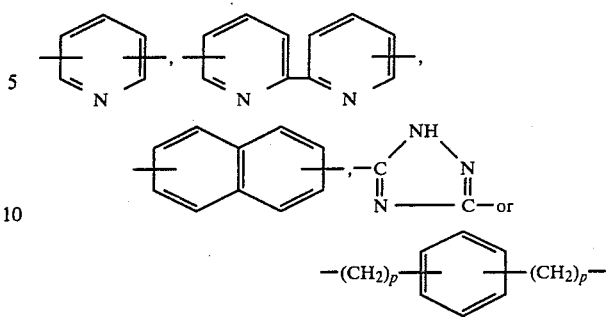

in which p represents an integer from 1 to 3. The symbol E can also include 2 to 5 phenylene or cyclohexylene radicals which are joined to one another by a single valence bond or by an inert atom or group such as —O—, —S—, an alkylene radical having from 1 to 3 carbon atoms, —CO—, —SO$_2$—, —NR$_{13}$—, —N=N—, —CONH—, —COO—, —P(O)R$_{12}$—, —CONH—X—NHCO—,

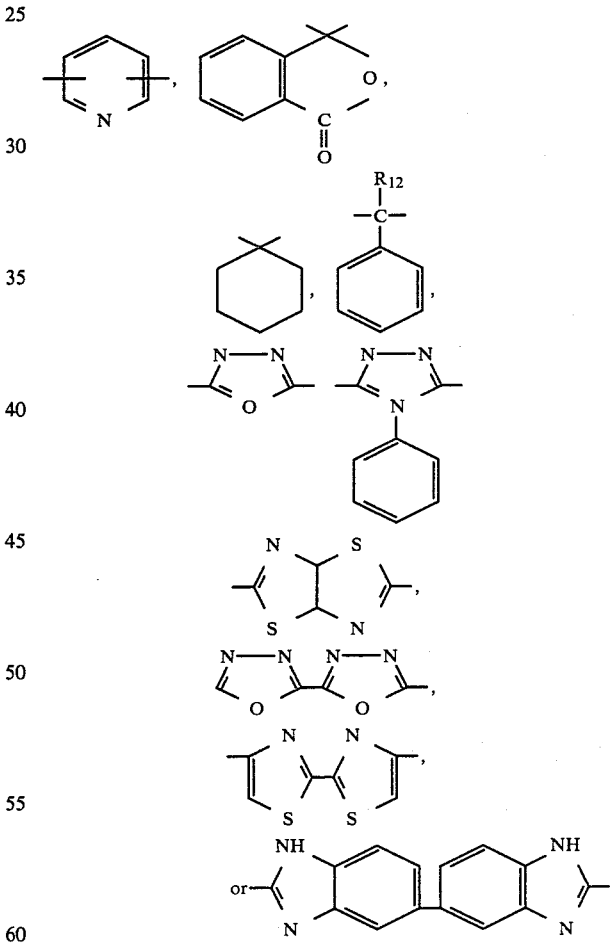

in which $R_{13}$ represents a hydrogen atom, an alkyl radical having from 1 to 4 carbon atoms or a phenyl or cyclohexyl radical and X represents an alkylene radical having fewer than 13 carbon atoms.

Exemplary of such diamines, there are mentioned as illustrative: 4,4'-diaminodicyclohexylmethane, 1,4-diaminocyclohexane, 2,6-diaminopyridine, metaphenylenediamine, paraphenylenediamine, 4,4'-diaminodiphenylmethane, 2,2-bis-(4-aminophenyl)-propane, benzidine, para-aminophenyl oxide, para-aminophenyl sulfide, 4,4'-diaminodiphenylsulfone, bis-(4-aminophenyl)-methylphosphine oxide, bis-(4-aminophenyl)-phenylphosphine oxide, bis- (4-aminophenyl)-methylamine, 1,5-diaminonaphthalene, meta-xylylenediamine, para-xylylenediamine, 1,1-bis-(para-aminophenyl)-phthalane, hexamethylenediamine, 6,6'-diamino-2,2'-bipyridyl, 4,4'-diaminobenzophenone, 4,4'-diaminoazobenzene, bis-(4-aminophenyl)-phenylmethane, 1,1-bis-(4-aminophenyl)-cyclohexane, 1,1-bis-(4-amino-3-methylphenyl)-cyclohexane, 2,5-bis-(m-aminophenyl)-1,3,4-oxadiazole, 2,5-bis-(p-aminophenyl)-thiazolo-[4,5-d]thiazole, 5,5'-di-(m-aminophenyl)-bis-(1,3,4-oxadiazolyl-2,2'), 4,4'-bis-(p-aminophenyl)-2,2'-bithiazole, m-bis-[4-(p-aminophenyl)-thiazol-2-yl]-benzene, 2,2'-bis-(m-aminophenyl)-5,5'-dibenzimidazole, 4,4'-diaminobenzanilide, phenyl 4,4'-diaminobenzoate, N,N,'-bis-(4-aminobenzoyl)-p-phenylenediamine, 3,5-bis-(m-aminophenyl)-4-phenyl-1,2,4-triazole, 4,4'-N,N'-bis-(p-aminobenzoyl)-diaminodiphenylmethane, bis-p-(4-aminophenoxycarbonyl)-benzene, bis-p-(4-aminophenoxy)-benzene, 3,5-diamino-1,2,4-triazole, 1,1-bis-(4-aminophenyl)-1-phenylethane and 3,5-bis-(4-aminophenyl)-pyridine. According to the invention, the aromatic diamines are the preferred.

Other than the bis-primary diamines, the polyamines of the formula [III] which are preferably used include those which have fewer than 50 carbon atoms and which possess from 3 to 5 —NH$_2$ groups per molecule. The —NH$_2$ groups can be borne by a benzene nucleus which is optionally substituted by methyl groups, or they can be borne by a naphthalene, pyridine or triazine nucleus; they can also be borne by several benzene nuclei which are joined to one another by a single valence bond or by an inert atom or group which can be one of those described above within the scope of the definition of the symbol E, or also

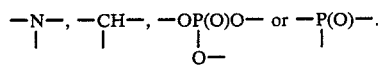

Examples of such polyamines are 1,2,4-triaminobenzene, 1,3,5-triaminobenzene, 2,4,6-triaminotoluene, 2,4,6-triamino-1,3,5-trimethylbenzene, 1,3,7-triaminonaphthalene, 2,4,4'-triaminobiphenyl, 2,4,6-triaminopyridine, 2,4,4'-triaminodiphenyl oxide, 2,4,4'-triaminodiphenylmethane, 2,4,4'-triaminodiphenylsulfone, 2,4,4'-triaminobenzophenone, 2,4,4'-triamino-3-methyldiphenylmethane, N,N,N-tris(4-aminophenyl)-amine, tris-(4-aminophenyl)-methane, 4,4',4''-triaminotriphenyl orthophosphate, tris-(4-aminophenyl)-phosphine oxide, 3,5,4'-triaminobenzanilide, melamine, 3,5,3',5'-tetraaminobenzophenone, 1,2,4,5-tetraaminobenzene, 2,3,6,7-tetraaminonaphthalene, 3,3'-diaminobenzidine, 3,3',4,4'-tetraaminodiphenyl oxide, 3,3',4,4'-tetraaminodiphenylmethane, 3,3',4,4'-tetraaminodiphenylsulfone, 3,5-bis-(3,4,-diaminophenyl)-pyridine and the oligomers of the average formula:

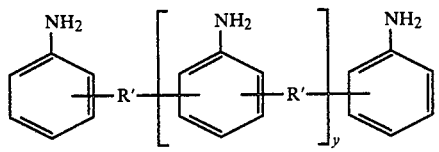

in which y represents a mean number ranging from about 0.1 to 2, the symbol R' denoting a divalent hydrocarbon radical which has from 1 to 8 carbon atoms and is derived from an aldehyde or ketone of the general formula:

$$O=R'$$

in which the oxygen atom is bonded to a carbon atom of the radical R'; typical aldehydes and ketones are formaldehyde, acetaldehyde, enanthaldehyde, benzaldehyde, acetone, methyl ethyl ketone, hexan-2-one, cyclohexanone and acetophenone. These oligomers containing amino groups can be obtained in accordance with known processes, such as those described in French Pat. Nos. 1,430,977, 1,481,935 and 1,533,696, hereby expressly incorporated by reference and relied upon; the crude mixtures of polyamines obtained in accordance with these processes can be enriched in one or more constituents, for example, by distillation under reduced pressure.

Among the monoamines of the formula [III], namely, those amines in which n=1, alkylamines, in particular butylamine, and arylamines, in particular aniline and mesidine (or 2,4,6-trimethyl-1-aminobenzene), toluidine and ortho-, meta- and para- chloroanilines, are noted as illustrative.

In the process of the invention, the proportions of acid (1) and salt (2) can vary over wide limits; the molar ratio of acid (2)/salt (2) is generally between 0.01 and 100, and preferably between 0.1 and 10. Furthermore the following ratios are defined:

$$r_1 = \frac{\text{total number of mols of acid (1) and salts (2)}}{\text{total number of NH}_2 \text{ groups in the amine of the formula [III] employed in the reaction}}$$

$$r_2 = \frac{\text{total number of mols of anhydride of the formula [II] employed in the reaction}}{\text{total number of NH}_2 \text{ groups in the amine of the formula [III] employed in the reaction}}$$

In general terms, it is advantageous to comply with the following conditions:
  $r_1$ is between 0.01 and 2, and preferably between 0.1 and 1, and
  $r_2$ is between 1 and 3, and preferably between 1.01 and 1.5.

If the process of the invention is carried out continuously, the number of mols of reactants and of constituents of the catalyst system which are to be taken into consideration are obviously the number of mols employed per unit time (namely, mean number of mols).

The reaction according to the invention is carried out in the liquid phase at temperatures which are generally between 80° and 180° C., and preferably between 100° and 150° C. The lower temperatures are of little value because the reaction is slow and the higher temperatures are likely to give rise to secondary reactions.

The process according to the invention can be carried out without solvent, i.e., either in the molten state or in the form of a solution in the reactants in the case where the latter are liquid under the operating conditions.

However, in accordance with a preferred process embodiment, the reaction is carried out in an organic solvent medium, the overall concentration of reactants and catalyst system generally being between 5 and 50%, and preferably between 10 and 40% (by weight).

Solvents which advantageously are utilized are liquid and inert under the process operating conditions, that is to say, they do not react to any appreciable extent with either the anhydride of the formula [II] or the amine of the formula [III]. The following are thus mentioned as illustrative: aliphatic or aromatic hydrocarbons, such as benzene, toluene, xylenes and ethylbenzene, aliphatic or aromatic hydrocarbons which are substituted by chlorine atoms, in particular chlorobenzene, methylene chloride, carbon tetrachloride, 1,2-dichloroethane and 1,1,2,2-tetrachloroethane, or which are substituted by other functional groups, such as benzonitrile, propionitrile, butyronitrile and ketones, polar aprotic solvents such as dimethylformamide and dimethylsulfoxide, and ethers such as diisobutyl ether, dimethoxyethane, diglyme (or diethylene glycol dimethyl ether) and anisole (or methoxybenzene).

From a practical point of view, various methods of operation can be adopted. In accordance with a simple method of operation, all of the reactants and catalysts are brought together in the reactor and heated to appropriate temperature. In accordance with another method of operation, which has the advantage in that it avoids secondary reactions as much as is possible, all or part of the anhydride of the formula [II] and of the catalyst system (1)/(2) are first introduced into the reactor and the amine of the formula [III] is then gradually introduced into the said reactor.

In accordance with a preferred method of operation, and with a view towards improving yields, the water is continuously removed from the reaction medium as it is formed. A convenient method for removing this water consists of continuously distilling the reaction medium, in condensing the distillate by cooling, in decanting this distillate which has condensed into two phases, one being aqueous and the other being essentially composed of the organic solvent used, in separating and removing the aqueous phase and in returning the organic phase to the top of the column.

At completion of the reaction, the oligo-imide of the formula [I], which is a product of the reaction, is separated by any known means. For example, it is possible to evaporate off the solvent and then carry out selective extractions using suitable solvents.

In accordance with an advantageous method, the process for the preparation of imide according to the invention is carried out in a solvent which is such that, at ambient temperature or at a lower temperature, the reactants and the catalyst system remain soluble (for the major part) whereas the oligo-imide is insoluble or at least is only slightly soluble (solubility preferably less than 5%). Under these conditions, the oligo-imide is isolated by simply cooling the reaction medium and filtering off the precipitate obtained; the filtrate, or mother liquors, contains solvent, the catalyst system and, possibly, excess anhydride which has not reacted and a small amount of oligo-imide which has not precipitated. This mixture can be re-used, as is, in order to form the basis for a new operation, i.e., it suffices to add the anhydride of the formula [II] to this mixture, to heat the entire mass to the desired temperature and then to gradually add the amine of the formula [III] under the aforesaid typical conditions.

The reaction times in the process of the invention can obviously vary over wide limits and depend especially on the temperature used; most frequently, same are between 0.3 and 5 hours, and, more particularly, are between 0.5 and 2 hours.

The process of the invention is particularly advantageous because of the ease with which it is carried out and the good performance which can thereby be achieved, as regards both the reaction rate and the yield of oligo-imide produced.

The oligo-imides obtained according to the invention are used, e.g., for the preparation of thermosetting resins. By reacting oligo-imides containing several imide functions (optionally in association with monoimides) with polyamines, the oligo-imides lead, in particular, to cross-linked polymers of high heat stability [French Pat. No. 1,555,564, hereby also expressly incorporated by reference].

The above process has been described using, as the starting materials, reactants consisting of anhydrides and amines. In fact, it is known that an anhydride and a primary amine condense rapidly and without difficulty to give an amic acid in accordance with the equation:

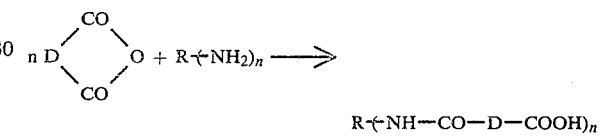

According to the invention, an oligo-imide is therefore normally prepared in two stages, one being the condensation of the reactants to yield an amic acid and the other being the cyclic dehydration of the amic acid to yield an imide according to the equation:

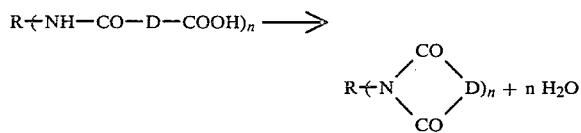

Therefore, it would not be outside the scope of the invention to first produce the amic acid from an anhydride and an amine of the formula [III] without a catalyst, and then, when this amic acid has been formed, to bring the catalyst system (1)/(2) together therewith, under the operating conditions defined above. A process of this kind can therefore be considered to be a simple variant of the general process described above, which variant, on the one hand, consists in replacing the anhydride and the amine with the amic acid, or which, on the other hand, consists in not introducing the catalyst system initially, but rather introducing same after the anhydride and the amine have begun to react.

In order to further illustrate the present invention and the advantages thereof, the following specific examples are given, it being understood that same are intended only as illustrative, and in nowise limitative. These examples illustrate the preparation of an imide using, as the starting materials, either an anhydride and an amine or an amic acid.

EXAMPLE 1

0.267 g (2.78 millimols) of methanesulfonic acid, 5.039 g (8.98 millimols) of tetraoctylammonium methanesulfonate, 15.157 g (154.7 millimols) of maleic anhydride and 60 cm$^3$ of ethylbenzene were introduced into a 250 cm$^3$ round-bottomed flask equipped with a stirrer and a distillation column.

A solution, heated to 80° C., which contained 80 cm$^3$ of ethylbenzene and 7.531 g (38.03 millimols) of 4,4'-diaminodiphenylmethane was added continuously and gradually thereto over the course of 20 minutes.

The temperature of the reaction medium increased gradually from 30° to 48° C. during this addition. This mixture was gradually heated to 133° C. over the course of 43 minutes; boiling begins at this temperature. The mixture was then distilled for 2 hours 7 minutes; the distillate was condensed and then decanted, the aqueous layer was removed and the ethylbenzene was returned to the top of the column.

The reaction mixture was cooled to 18° C. The precipitate was filtered off, washed 3 times with, each time, 10 cm$^3$ of ethylbenzene at 18° C. and then dried at ambient temperature (23° C.) under a pressure which was reduced to 1 mm Hg (absolute pressure).

12.6435 g of a product having a melting point of 157° C. and containing (polarographic determination) 91.5% of 4,4'-bis-(maleimido)-diphenylmethane were thus obtained.

A further 3.77 millimols of 4,4'-bis-(maleimido)-diphenylmethane were found in the mother liquor from filtration.

EXAMPLE 2

0.296 g (3.02 millimols) of methanesulfonic acid, 5.614 g of a dimethyldialkylammonium methanesulfonate, the alkyl chains in this salt being linear chains containing 16 or 18 carbon atoms, 15.041 g (153.5 millimols) of maleic anhydride and 60 cm$^3$ of ethylbenzene were introduced into a 250 cm$^3$ round-bottomed flask equipped with a stirrer and a distillation column.

A solution, heated to 80° C., which contained 70 cm$^3$ of ethylbenzene and 7.512 g (37.94 millimols) of 4,4'-diamino-diphenylmethane was added continuously and gradually thereto over the course of 14 minutes.

The mixture was then heated gradually to 133.5° C. over the course of 46 minutes; distillation began from this temperature and required 1 hour 50 minutes. The reaction medium was distilled and treated as in Example 1.

12.588 g of a product containing (polarographic determination) 91.5% of 4,4'-bis-(maleimido)-diphenylmethane were obtained; the mother liquor from filtration contained 3.58 millimols of 4,4'-bis-(maleimido)-diphenylmethane.

The 4,4'-bis-(maleimido)-diphenylmethane obtained was recrystallized. 5.04 g of this compound were dissolved in 50 cm$^3$ of ethylbenzene at 120° C.; the solution was filtered hot and then cooled to 20° C. The crystals obtained were filtered off and washed 3 times with 5 cm$^3$ of ethylbenzene; after drying, 4.52 g of a product containing 95.4% of 4,4'-bis-(maleimido)-diphenylmethane were obtained.

EXAMPLE 3

0.4875 g (3.09 millimols) of benzenesulfonic acid, 5.666 g (9.09 millimols) of tetraoctylammonium benzenesulfonate, 15.012 g (153.1 millimols) of maleic anhydride and 60 cm$^3$ of ethylbenzene were introduced into a 250 cm$^3$ round-bottomed flask equipped with a stirrer and a distillation column.

A solution, heated to 80° C., which contained 70 cm$^3$ of ethylbenzene and 7.546 g (38.1 millimols) of 4,4'-diamino-diphenylmethane, was added continuously and gradually thereto over the course of 6 minutes.

The mixture was then gradually heated to 133° C. over the course of 34 minutes and then distilled for 88 minutes. The reaction mixture was distilled and treated as in Example 1.

13.0635 g of a product containing (polarographic determination) 93.6% of 4,4'-bis-(maleimido)-diphenylmethane were obtained; the mother liquor from filtration contained 3.07 millimols of 4,4'-bis-(maleimido)-diphenylmethane.

EXAMPLE 4

0.616 g (0.0039 mol) of benzenesulfonic acid, 8.243 g (0.0114 mol) of dimethyloctadecylammonium benzenesulfonate (purity: 98.2%), 30.036 g (0.3065 mol) of maleic anhydride and 85 cm$^3$ of chlorobenzene were introduced into the apparatus described in Example 1.

This mixture was stirred mechanically and a solution, maintained at 100° C., which contained 19.86 g (0.1003 mol) of 4,4'-diaminodiphenylmethane and 88 cm$^3$ of chlorobenzene, was added continuously thereto over the course of 13 minutes.

After mixing, the temperature was 54° C. The medium was heated and distilled as in Example 1. Distillation was carried out for 2 hours 8 minutes and the temperature of the reaction mixture increased from 127° C. to 131° C. Upon completion of the distillation, the medium consisted of a homogeneous liquid. It was then cooled to a temperature of 20° C. The crystalline precipitate obtained was filtered off, washed 3 times with 25 cm$^3$ of chlorobenzene each time, and then dried at ambient temperature (25° C.) under a reduced pressure of 1 mm Hg (absolute pressure).

29.503 g of a product having a melting point of 159.5° C. and containing 99.5% of 4,4'-bis-(maleimido)-diphenylmethane (determined by polarography) were thus obtained.

0.018 mol of 4,4'-bis-(maleimido)-diphenylmethane was found, by polarographic analysis, in the mother liquor from the filtration.

EXAMPLE 5

2.210 g (0.0230 mol) of methanesulfonic acid, 15 g (0.0666 mol) of tetraethylammonium methanesulfonate, 33.4 g (0.340 mol) of maleic anhydride and 75 cm$^3$ of 1,2-dichloroethane were introduced into the apparatus described in Example 1.

The medium was heated to the boiling point and mechanically stirred. A solution containing 22.556 g (0.1139 mol) of 4,4'-diaminodiphenylmethane and 130 cm$^3$ of 1,2-dichloroethane was continuously added over the course of 22 minutes.

The medium was distilled (83° C.) as in Example 1, while the water of reaction was continuously removed. The distillation required 10 hours.

Only half of the reaction mixture was treated. 154.45 g of this reaction medium were, therefore, washed 5 times with 30 cm$^3$ of water each time; the organic phase was dried over anhydrous magnesium sulfate, filtered and evaporated to dryness; the residue was washed with ethyl ether, drained and dried. A light yellow product having a melting point of 159° C. and containing 99%

(polarographic determination) of 4,4'-bis-(maleimido)-diphenylmethane was thus obtained. The chemical yield relative to reacted diaminodiphenylmethane was 99%.

EXAMPLE 6

1.473 g (0.0153 mol) of methanesulfonic acid, 10.0 g (0.0444 mol) of tetraethylammonium methanesulfonate, 22.3 g (0.227 mol) of maleic anhydride and 80 cm³ of 1,1,2,2-tetrachloroethane were introduced into the equipment described in Example 1.

The medium was heated to the boiling point (147.5° C.) and mechanically stirred. A solution containing 15.013 g (0.0758 mol) of 4,4'-diaminodiphenylmethane and 30 cm³ of 1,1,2,2-tetrachloroethane was continuously added thereto over the course of 6 minutes.

The medium was then distilled as in Example 1 for an additional 9 minutes.

The resulting reaction mixture was cooled to 20° C. and washed successively, 3 times, with 25 cm³ of water. The resulting organic phase was dried over anhydrous magnesium sulfate and concentrated in vacuo. The oily liquid product obtained was added into 100 cm³ of ether and this caused a yellow crystalline product to precipitate. This product was filtered off, washed with ether and dried. 27.35 g of a solid containing 95.4% of 4,4'-bis-(maleimido)-diphenylmethane and melting at 159° C. were obtained.

EXAMPLE 7

0.146 g (0.00152 mol) of methanesulfonic acid, 0.857 g (0.0038 mol) of tetraethylammonium methanesulfonate, 22.3 g (0.227 mol) of maleic anhydride and 45 cm³ of CHCl₂—CHCl₂ were introduced into the apparatus described in Example 1.

The medium was heated to the boiling point and mechanically stirred. A solution containing 15.062 g (0.0760 mol) of 4,4'-diaminodiphenylmethane and 50 cm³ of CHCl₂—CHCl₂ was continuously added thereto over the course of 13 minutes.

The medium was then distilled as in Example 1 for an additional 1 hour 51 minutes.

The reaction mixture was then treated as in Example 5 and this yielded a solid yellow product weighing 26.95 g and containing, by polarographic analysis, 93.9% of 4,4'-bis-(maleimido)-diphenylmethane.

EXAMPLE 8

0.0495 g (0.516 mM) of methanesulfonic acid, 0.462 g (2.05 mM) of tetraethylammonium methanesulfonate and 160 g of chlorobenzene were introduced into a 250 cm³ round-bottomed flask equipped with a stirrer and a distillation column. (mM is an abbreviation for millimol.)

The mixture was distilled at 132° C., the water being removed and the organic phase of the condensed distillate being recycled. 1.046 g (5.10 millimols) of N-(para-tolyl)-maleamic acid were then added. The distillation operation at 132° C. was then repeated and the water produced by the reaction was removed. After 150 minutes, the reaction was terminated and the solution was analyzed by polarography. It was found that all the maleamic acid had been converted and that 5.0 millimols of N-tolyl-maleimide had been produced. (The chemical yield relative to reacted maleamic acid was 98%.)

EXAMPLE 9

In the apparatus described in Example 7, the same operation was repeated, but using the following amounts: 0.571 g (2.93 mM) of p-toluenesulfonic acid (1H₂O), 2.690 g (8.94 mM) of tetraethylammonium p-toluenesulfonate, 1.026 g (5.0 mM) of N-(para-tolyl)-maleamic acid and 155.713 g of chlorobenzene.

After a reaction time of 35 minutes at 132° C., a portion of the reaction mixture (131 g) was cooled to 20° C. and washed 5 times with 20 cm³ of water. The organic solution was then dried by contact with anhydrous magnesium sulfate and evaporated to dryness. A crystalline product was obtained which weighed 0.7844 g, had a melting point of 150° C. and displayed infra-red and NMR spectra which were identical to those of N-tolylmaleimide. A determination of polarographic analysis, using a pure product as the reference, reflected a content of 93.4%. (Chemical yield relative to reacted maleamic acid: 94%.)

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of an oligoimide, comprising reacting a dicarboxylic acid anhydride with a amine, said anhydride being represented by the formula:

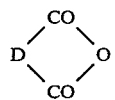

[II]

and said amine being represented by the formula:

R—(—NH₂)$_n$    [III]

in which formulae n is a positive integer which is less than or equal to 5, R is an organic radical of valency n, having not greater than 50 carbon atoms, and D represents a divalent radical selected from the group consisting of

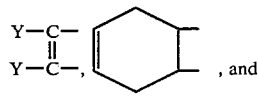, and 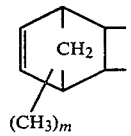

in which m is equal to 0 or 1 and Y represents hydrogen, chlorine or methyl, said reaction being carried out in the presence of a catalyst system comprising a mixture of a compound (1) and a compound (2), (1) being a strong inorganic or organic acid having at least one oxygen atom present thereon and which possesses at least one acid functionality having an ionization constant in water which is not greater than 3, and (2) being an ammonium salt of said acid, the cationic ammonium moiety of said salt being at least di-N-substituted by organic radicals.

2. The process of claim 1 wherein the cationic ammonium moiety of said ammonium salt is represented by the structural formula selected from the group consisting of:

(1) $R_4 - \overset{R_1}{\underset{R_3}{\overset{|}{\underset{|}{N}}}} - R_2$  [IV]

wherein $R_1$, $R_2$, $R_3$, and $R_4$ which can be the same or different independently represent a member selected from the group consisting of hydrogen, and organic radicals in which the free valency is borne by a carbon atom, said organic radicals being selected from at least one member of the group consisting of (a) aliphatic; (b) cycloaliphatic; (c) aromatic; (d) arylaliphatic; and (e) those represented by the structural formula:

$$-R_5 +O-R_5 \frac{1}{t} OH \quad [V]$$

wherein t can vary between 1 and 10; and $R_5$ is a radical selected from the group consisting of $-CH_2-$, $-CH_2-CH_2-$, and $$-CH_2-\underset{CH_3}{\overset{|}{CH}}-$$

and wherein not greater than two of any one of said $R_1$ to $R_4$ groups is hydrogen; and (2) $\underset{R_8}{\overset{R_6}{\diagdown}} N - R_{12} - N \underset{R_{11}}{\overset{R_9}{\diagup}}$  [VI]

wherein $R_6$, $R_7$, $R_8$, $R_9$, $R_{10}$, and $R_{11}$ represent the organic radicals defined in structural formula [IV] for $R_1$, $R_2$, $R_3$, and $R_4$, and $R_{12}$ is a divalent organic radical having the free valencies thereon borne by aliphatic carbon atoms, said $R_{12}$ radical being selected from the group consisting of aliphatic, arylaliphatic, and aliphatic or arylaliphatic radicals wherein the aliphatic carbon atoms thereof are interrupted by at least one oxygen atom.

3. The process as defined by claim 1, wherein said salt (2) is a quaternary ammonium salt.

4. The process as defined by claim 1, wherein said strong oxygen-containing acid (1) has an ionization constant, in water, which is less than or equal to 3.

5. The process as defined by claim 4, wherein said acid is selected from the group consisting of sulfuric, phosphoric, organo-sulfonic, organo-phosphonic and halogen-containing carboxylic acids.

6. The process as defined by claim 5, wherein said acid is methanesulfonic acid, para-toluenesulfonic acid or benzenesulfonic acid.

7. The process as defined by claim 1, wherein said ammonium salt (2) comprises a tetravalent nitrogen atom substituted by either the same or different organic radicals wherein the free valency of each is borne by a carbon atom.

8. The process as defined by claim 7, wherein any two or more of the N-substituents combine to form a single divalent substituent, a single trivalent substituent, or two individual divalent substituents.

9. The process as defined by claim 1, wherein the total number of carbon atoms in the cationic moiety comprising the ammonium salt is less than 50.

10. The process as defined by claim 9, the said total number of carbon atoms being between 6 and 42.

11. The process as defined by claim 1, wherein the anhydride is maleic anhydride and the amine is 4,4'-diaminodiphenylmethane, or 4,4'-diaminodiphenyl ether, or 4,4'-diaminodiphenylsulfone.

12. The process as defined by claim 1, wherein the molar ratio of acid (1) salt (2) is between 0.01 and 100, the ratio of the number of mols of acid (1) and the salt (2) to the number of $NH_2$ groups in the amine of the formula [III] is between 0.01 and 2, and the ratio of the number of mols of anhydride of the formula [II] to the number of $NH_2$ groups in the amine of the formula [III] is between 1 and 3.

13. The process as defined by claim 12, said molar ratio of acid (1)/salt (2) being between 0.01 and 10, the ratio of number of mols acid and salt to the number of $NH_2$ groups in the amine being between 0.1 and 1, and the ratio of the number of mols of anhydride to the number of $NH_2$ groups in the amine being between 1.01 and 1.5.

14. The process as defined by claim 1, wherein the temperature of reaction is between 80° and 180° C., and the reaction is conducted in a solvent medium such that water of reaction is removed as it is formed.

15. The process as defined by claim 1, wherein the reaction is conducted in a solvent medium such that, at ambient temperature, the reactants and the catalyst system remain predominantly soluble, whereas the oligo-imide is insoluble or only slightly soluble.

16. The process as defined by claim 1, wherein at least a portion of the anhydride and the amine are replaced by an amic acid of the formula:

$$R+NH-CO-D-COOH)_n$$

wherein n is a positive integer which is less than or equal to 5, R is an organic radical of valency n, containing up to 50 carbon atoms, and D represents a divalent radical selected from the group consisting of $\underset{Y-C-}{\overset{Y-C-}{\underset{\|}{\|}}}$⟨hexagon⟩ and ⟨hexagon with $CH_2$⟩$(CH_3)_m$ in which m is equal to 0 or 1 and Y represents hydrogen, chlorine or methyl.

17. The process as defined by claim 1, wherein the cation of the ammonium salt (2) is selected from the group consisting of tetramethylammonium, tetraethylammonium, tetrapropylammonium, tetrahexylammonium, tetraoctylammonium, tetradodecylammonium, tetrabutylammonium, tributyldodecylammonium, trimethyldodecylammonium, trimethyltetradecylammonium, trimethylhexadecylammonium, trimethyloctadecylammonium, trimethyloctadecen-9-ylammonium, trimethyloctadien-9,12-ylammonium, trimethyloctadecatrien-9,12,15-ylammonium, trimethyleicosylammonium, trimethyldocosylammonium, trimethyldocosen-13-ylammonium, triethyloctadecylammonium, triethylhexylammonium, dimethylbenzyldodecylammonium, diethylbenzyldodecylammonium, dimethyldioctadecylammonium, diethyldioctadecylammonium, dimethylditetradecylammonium, diethylditetradecylammonium, dimethyldidodecylammonium, diethyldidodecylammonium, dimethyldihexadecylammonium, methyltributylammonium, methyltriethylammonium, methyltridodecylammonium, ethyltributylammonium, ethyltrioctylammonium, and ethyltridodecylammonium.

18. The process as defined by claim 17, wherein the anhydride is selected from the group consisting of maleic anhydride, chloromaleic anhydride, citraconic anhydride, tetrahydrophthalic anhydride or endomethylenetetrahydrophthalic anhydride.

19. The process as defined by claim 18, wherein the amine has the formula $RNH_2$, wherein R is a monovalent organic radical containing up to 50 carbon atoms.

20. The process as defined by claim 18, wherein the amine is selected from the group consisting of 4,4'-diaminodicyclohexylmethane, 1,4-diaminocyclohexane, 2,6-diaminopyridine, metaphenylenediamine, paraphenylenediamine, 4,4'-diaminodiphenylmethane, 2,2-bis-(4-aminophenyl)-propane, benzidine, paraaminophenyl oxide, para-aminophenyl sulfide, 4,4'-diaminodiphenyl-sulfone, bis-(4-aminophenyl)-methylphosphine oxide, bis-(4-aminophenyl)-phenylphosphine oxide, bis-(4-aminophenyl)-methylamine, 1,5-diaminonaphthalene, meta-xylylenediamine, para-xylylenediamine, 1,1-bis-(para-aminophenyl)-phthalene, hexamethylenediamine, 6,6'-diamino2,2'-bipyridyl, 4,4'-diaminobenzophenone, 4,4'-diaminoazobenzene, bis-(4-aminophenyl)-phenylmethane, 1,1-bis-(4-aminophenyl)-cyclohexane, 1,1-bis-(4-amino-3-methylphenyl)-cyclohexane, 2,5-bis-(m-aminophenyl-1,3,4-oxadiazole, 2,5-bis-(p-aminophenyl)-thiazolo-[4,5-d]thiazole, 5,5'-di-(m-aminophenyl)-bis-(1,3,4-oxadiazolyl-2,2'), 4,4'-bis-(p-aminophenyl-2,2'-bithiazole, m-bis-[4-(p-aminophenyl)-thiazol-2-yl]-benzene, 2,2'-bis-(m-aminophenyl)-5,5'-dibenzimidazole, 4,4'-diaminobenzanilide, phenyl 4,4'-diaminobenzoate, N,N,'-bis-(4-aminobenzoyl)-p-phenylenediamine, 3,5-bis-(m-aminophenyl)-4-phenyl-1,2,4-triazole, 4,4'-N,N'-bis-(p-aminobenzoyl)-diaminodiphenylmethane, bis-p-(4-aminophenoxycarbonyl)-benzene, bis-p-(4-aminophenoxy)-benzene, 3,5-diamino-1,2,4-triazole, 1,1-bis-(4-aminophenyl)-1-phenylethane, 3,5-bis-(4-aminophenyl)-pyridine, 1,2,4-triaminobenzene, 1,3,5-triaminobenzene, 2,4,6-triaminotoluene, 2,4,6-triamino-1,3,5-trimethylbenzene, 1,3,7-triaminonaphthalene, 2,4,4'-triaminobiphenyl, 2,4,6-triaminopyridine, 2,4,4'-triaminodiphenyl oxide, 2,4,4'-triaminodiphenylmethane, 2,4,4'-triaminodiphenylsulfone, 2,4,4'-triaminobenzophenone, 2,4,4'-triamino-3-methyldiphenylmethane, N,N,N-tris(4-aminophenyl)-amine, tris-(4-aminophenyl)-methane, 4,4',4''-triaminotriphenyl orthophosphate, tris-(4-aminophenyl)-phosphine oxide, 3,5,4'-triaminobenzanilide, melamine, 3,5,3',5'-tetraaminobenzophenone, 1,2,4,5-tetraaminobenzene, 2,3,6,7-tetraaminonaphthalene, 3,3'-diamonobenzidine, 3,3',4,4'-tetraaminodiphenyl oxide, 3,3',4,4'-tetraaminodiphenylmethane, 3,3',4,4'-tetraaminodiphenylsulfone, 3,5-bis-(3,4-diaminophenyl)-pyridine, and the oligomers of the formula:

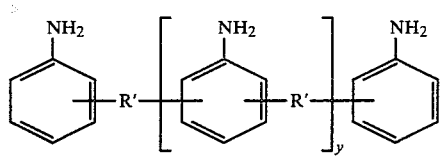

in which y represents a mean number ranging from about 0.1 to 2, and R' is a divalent hydrocarbon radical which has from 1 to 8 carbon atoms.

21. The process as defined by claim 19, wherein the amine is an alkylamine or an arylamine.

* * * * *